(12) United States Patent
Liu et al.

(10) Patent No.: US 6,627,743 B1
(45) Date of Patent: Sep. 30, 2003

(54) 6-O-METHYLERYTHROMYCIN A CRYSTAL FORM III

(75) Inventors: Jih-Hua Liu, Green Oaks, IL (US); Rodger F. Henry, Park City, IL (US); Stephen G. Spanton, Green Oaks, IL (US); David A. Riley, Kenosha, WI (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 09/454,366

(22) Filed: Dec. 3, 1999

(51) Int. Cl.$^7$ ............................. C07H 1/00; C07H 17/08
(52) U.S. Cl. ......................... 536/7.2; 536/7.4; 536/18.5; 536/127
(58) Field of Search ....................... 536/7.2, 127, 18.5, 536/7.4; 574/29

(56) References Cited

U.S. PATENT DOCUMENTS

| | | | |
|---|---|---|---|
| 4,331,803 A | 5/1982 | Watanabe et al. | 536/7.2 |
| 4,670,549 A | 6/1987 | Morimoto et al. | 536/7.4 |
| 4,672,109 A | 6/1987 | Watanabe et al. | 536/7.2 |
| 4,808,411 A | 2/1989 | Lu et al. | 424/441 |
| 4,990,602 A | 2/1991 | Morimoto et al. | 536/7.4 |
| 5,274,085 A | 12/1993 | Amano et al. | 536/7.4 |
| 5,556,839 A | 9/1996 | Greene et al. | 514/29 |
| 5,844,105 A | 12/1998 | Liu et al. | 536/18.5 |
| 5,858,986 A | 1/1999 | Liu et al. | 514/29 |
| 5,945,405 A | 8/1999 | Spanton et al. | 514/29 |

FOREIGN PATENT DOCUMENTS

| | | |
|---|---|---|
| EP | 0260938 | 12/1992 |
| EP | 0 559 896 | 8/1997 |
| WO | 9719096 | 5/1997 |
| WO | 9804573 | 2/1998 |
| WO | 9804574 | 2/1998 |

OTHER PUBLICATIONS

Adachi, et al., "Crystal and Molecular Structure of (14R)–14–Hydroxy–6–O–Methylerythromycin A", *The Journal of Antibiotics*, vol. XLII(6), Jun. 1989, pp. 1012–1014.

Iwasaki, et al., "Structure of 6–O–Methylerthromycin A (Clarithromycin)",*Acta Crystallograhica*, vol. c49(5), May 1993, pp. 1227–1230.

Kim, et al., "Conformational Study of Erythromycin Analogues", *Quantitative Structure–Activity Relationships in Drug Design*, vol. 291, 1989, pp. 325–328.

Primary Examiner—Elli Peselev
(74) Attorney, Agent, or Firm—B. Gregory Donner

(57) ABSTRACT

The present invention relates to a novel 6-O-methylerythromycin A crystal form, a process for preparing the crystal form, and methods for using the crystal form to prepare a 6-O-methylerythromycin A crystal form II.

6 Claims, 4 Drawing Sheets

6-O-METHYLERYTHROMYCIN A CRYSTAL FORM III

TECHNICAL FIELD OF INVENTION

The present invention relates to a novel 6-O-methylerythromycin A crystal form, a process for preparing the crystal form, and a method for using the crystal form to prepare a 6-O-methylerythromycin A crystal form II.

BACKGROUND OF THE INVENTION

6-O-methylerythromycin A (Clarithromycin) is a semi-synthetic macrolide antibiotic of the formula:

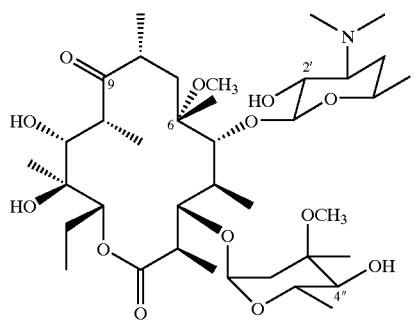

which exhibits excellent antibacterial activity against gram-positive bacteria, some gram-negative bacteria, anaerobic bacteria, Mycoplasma, and Chlamydia. The compound has demonstrated useful properties as a therapeutic agent for infections of the upper respiratory tract in children and adults.

The crystalline form of a compound can exist as different crystal forms (or polymorphs), which differ in the way the molecules are arranged and packed in the crystal lattice. Previously, the 6-O-methylerythromycin A compound has been reported in the literature as existing in at least three distinct crystal forms. For the sake of identification, these crystal forms have been designated "Form 0", "Form I", and "Form II." The unique physical properties of each crystal form is reflected in their infrared spectrum, powder X-ray diffraction pattern, and/or differential scanning crystallography (DSC), by which each crystal form can be individually indentified.

Form I of 6-O-methylerythromycin A was prepared according to the methods as described in U.S. Pat. No. 5,858,986, issued on Jan. 12, 1999, and first identified as exhibiting the X-ray powder diffraction pattern having the 2-theta angles 5.16°±0.2, 6.68°±0.2, 10.20°±0.2, 12.28°±0.2, 14.20°±0.2, 15.40°±0.2, 15.72°±0.2, and 16.36°±0.2.

The process for preparing Form II, which is the marketed crystal form of 6-O-methylerythromycin A, was disclosed in U.S. Pat. No. 5,844,105, issued on Dec. 1, 1998. The Form II X-ray powder diffraction pattern was identified as the following, wherein the 2-theta angles are 8.52°±0.2, 9.48°±0.2, 10.84°±0.2, 11.48°±0.2, 11.88°±0.2, 12.36°±0.2, 13.72°±0.2, 14.12°±0.2, 15.16°±0.2, 16.48°±0.2, 16.92°±0.2, 17.32°±0.2, 18.08°±0.2, 18.40°±0.2, 19.04°±0.2, 19.88°±0.2, and 20.48°±0.2.

Form 0 exists as a solvate of 6-O-methylerythromycin A. The identification and methods for preparing the isolated form Form 0 solvate are first described in the U.S. Pat. No. 5,945,405, which issued on Aug. 31, 1999. The representative X-ray powder diffraction pattern of the Form 0 solvate comprises the 2-theta angles 4.851°±0.2, 6.498°±0.2, 7.615°±0.2, 9.169°±0.2, 10.154°±0.2, 11.009°±0.2, 11.618°±0.2, 12.495°±0.2, 13.772°±0.2, 14.820°±0.2, 16.984°±0.2, 18.221°±0.2, 18.914°±0.2, and 19.495°±0.2.

The Form 0 solvate can be prepared by the recrystallization of 6-O-methylerythromycin A in a suitable solvent, such as ethanol, isopropyl acetate, isopropanol, and tetrahydrofuran. At temperatures of about room temperature up to about 50° C., the solvent molecules are released from the crystal lattice of Form 0 and the resulting crystal structure corresponds to Form I. Form I converts into Form II at controlled temperatures of from about 100–105° C. Conversion of the Form 0 crystal solvate into a Form II crystal is accomplished via a Form I intermediate. The Form 0, Form I and Form II crystal structures have been each been identified as an orthorhombic crystal system.

It has been unexpectedly discovered that 6-O-methylerythromycin A can be prepared as a new crystalline polymorph. The new crystal structure of 6-O-methylerythromycin A is an acetonitrile solvate of 6-O-methylerythromycin A. The novel polymorph can be used as an intermediate to prepare a pharmaceutically acceptable 6-O-methylerythromycin A Form II crystal.

SUMMARY OF THE INVENTION

In one aspect, the invention relates to a novel crystal solvate of 6-O-methylerythromycin A, which is designated for the sake of identification as the Form III crystalline polymorph. The polymorph exists as a solvate, and can be represented by the structure

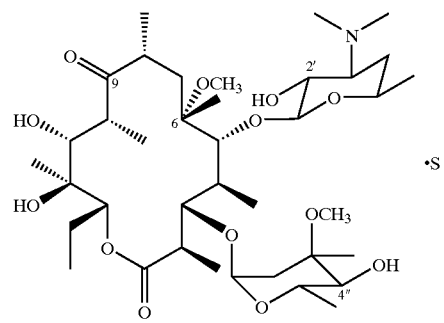

wherein S is one, two or three acetonitrile solvent molecules. The polymorph can exist in a mixture with other forms of 6-O-methylerythromycin A or in a substantially pure form having at least 90% Form III polymorph.

Substantially pure Form III exhibits a characteristic X-ray powder diffraction pattern 9.05°±0.2, 9.64°±0.2, 11.80°±0.2, 12.77°±0.2, 15.28°±0.2, 16.04°±0.2, 16.55°±0.2, 17.70°±0.2, 18.17°±0.2, 18.79°±0.2, and 24.94°±0.2. The crystal structure can be identified as a monoclinic crystal system. The crystallographic unit cell parameters of a single acetonitrile solvate crystal have been determined as having the following parameters: a is 10.591 (1) Å; b is 18.036 (1) Å; c is 11.555 (1) Å; and β is 95.72 (1)° to afford a cell volume of 2196.2 (3) Å$^3$, wherein a, b and c are each a representative length of the crystal lattice and P is the diagonal.

In another aspect, the invention relates to a process for preparing a substantially pure Form III polymorph. The Form III polymorph can be prepared by treating 6-O-methylerythromycin A with acetonitrile to obtain a homogeneous solution; allowing the solution to equilibrate at ambient temperature; cooling the solution to a temperature of 0–5° C. to form a solid precipitate in solution; and collecting the solid precipitate.

Yet another aspect of the invention relates to a process for preparing Form II of 6-O-methylerythromycin A from a substantially pure Form III polymorph. The process comprises drying a Form III polymorph at a temperature from about 80° C. to about 180° C. and isolating 6-O-methylerythromycin crystal Form II. Preferably, the process is accomplished at temperatures from about 90° C. to about 105° C.

Therefore, the invention provides novel crystal forms from which to obtain the 6-O-methylerythromycin product.

DETAILED DESCRIPTION OF THE INVENTION

Figure 1:
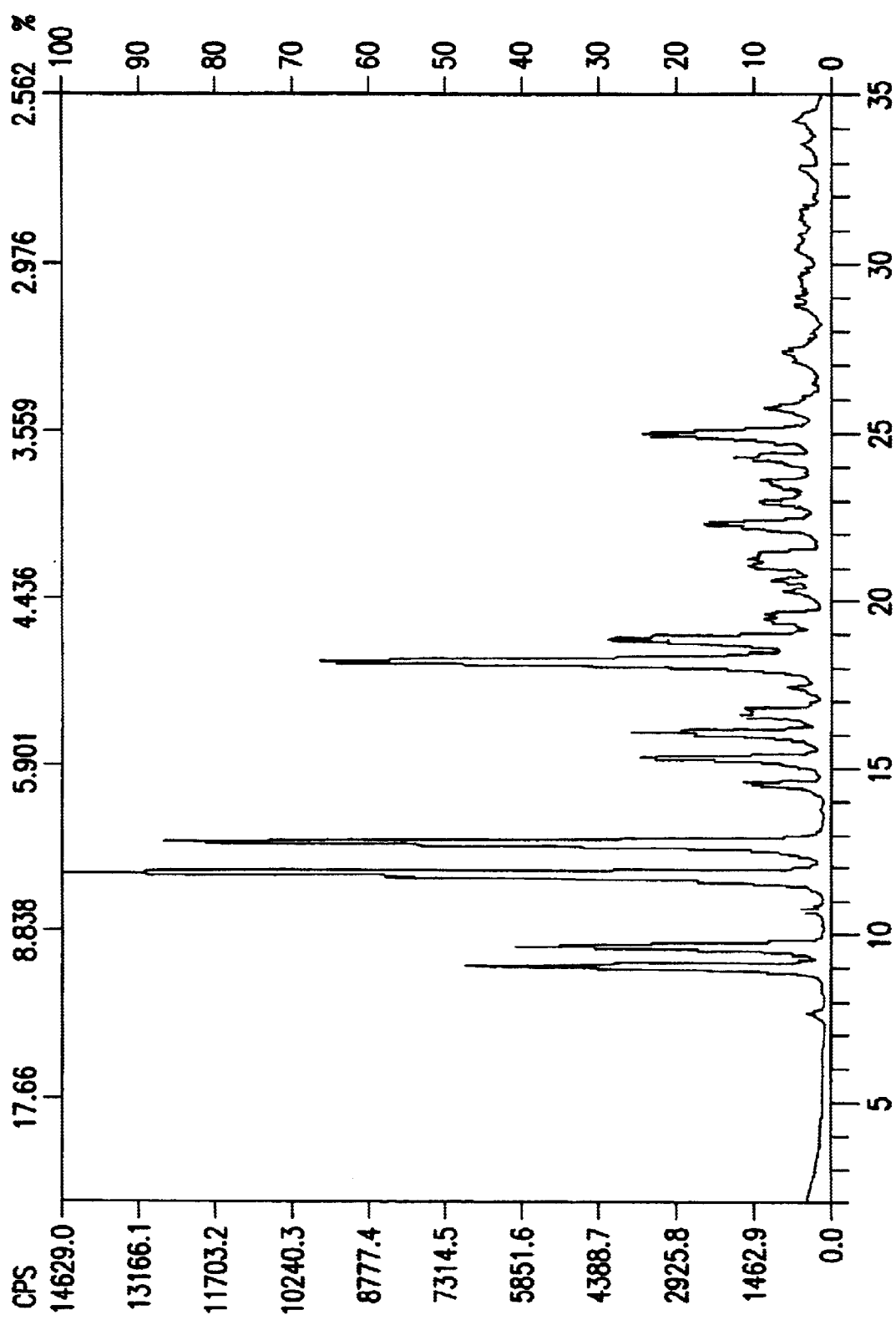
FIG. 1 is a graphical illustration of the powder X-ray diffraction spectrum of the 6-O-methylerythromycin A acetonitrile solvate.
Figure 2:
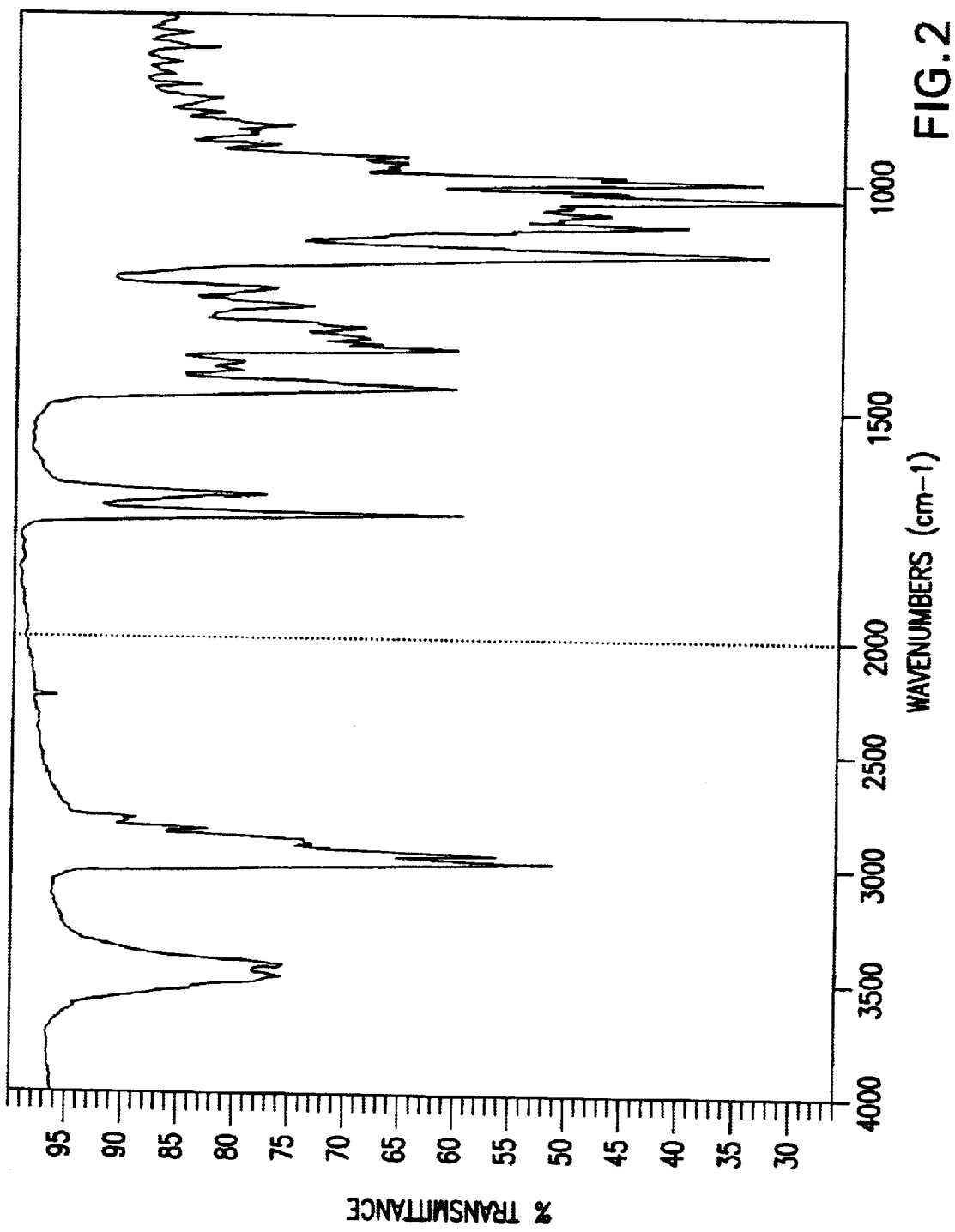
FIG. 2 is a graphical illustration of the mid-infrared spectrum of the 6-O-methyl-erythromycin A acetonitrile solvate.
Figure 3:
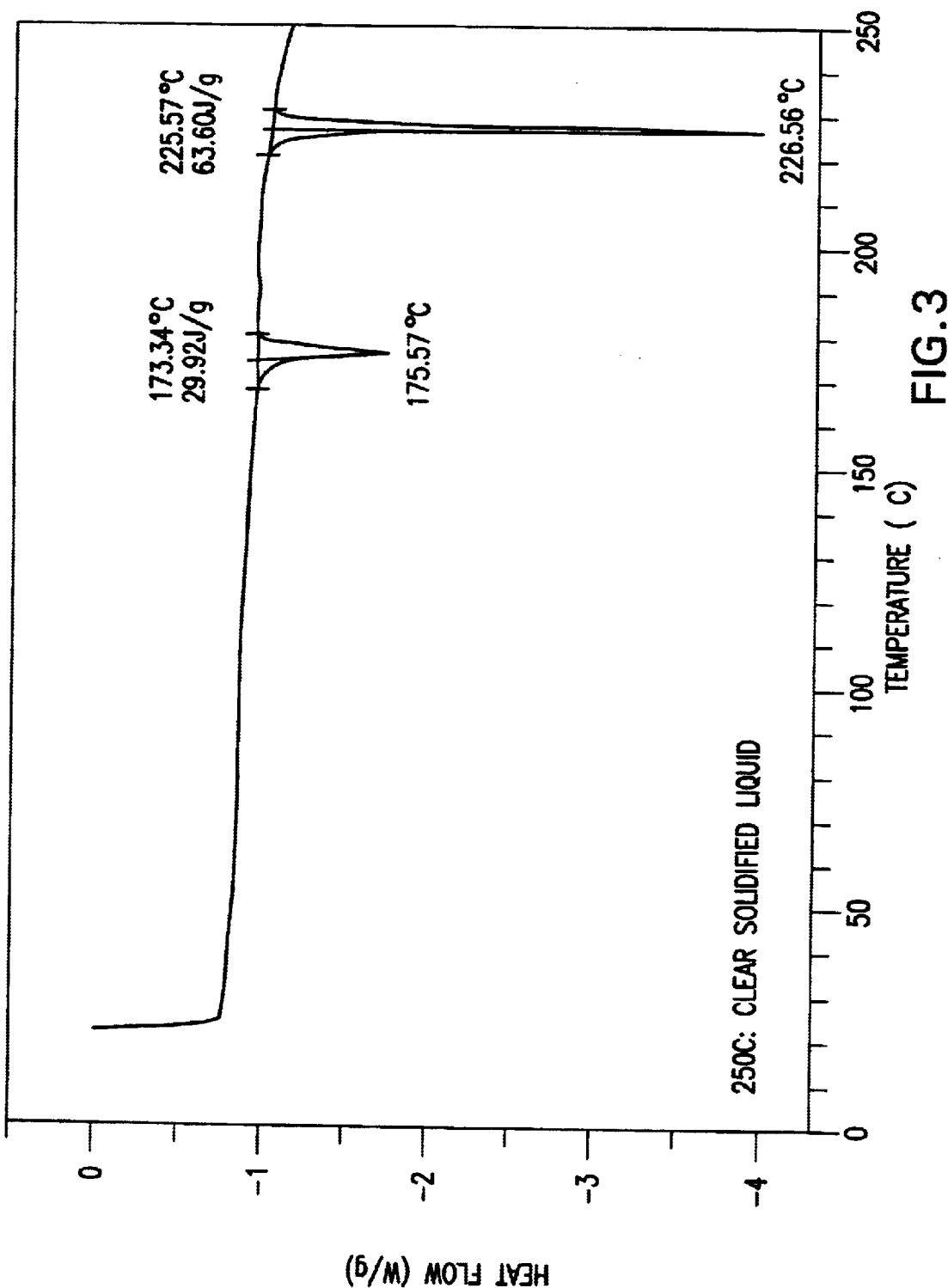
FIG. 3 is a graphical illustration of the differential scanning calorimetric (DSC) thermogram of 6-O-methylerythromycin A acetonitrile solvate.

As used herein, the term "substantially pure", when used in reference to a polymorph, refers to an identified polymorph, wherein the polymorph has at least 90% purity. For the sake of clarification, the phrase "at least 90% purity" refers to a desired polymorph containing no more than 10% of any other compound and, in particular, containing more than 10% of any other polymorph. It is preferred that the desired "substantially pure" polymorph has 5% or less of any other compound or polymorph. More preferably, the desired "substantially pure" polymorph has 3% or less of any other compound or polymorph.

The commercially available 6-O-methylerythromycin A starting material can be obtained from Abbott Laboratories, Abbott Park, Ill., U.S.A. The compound can also be synthesized by methylation of erythromycin A (also available from Abbott Laboratories) via a suitable erythromycin derivative. Various methods for preparing 6-O-methylerythromycin A have been described in the literature. Examples of syntheses suitable for the preparation of 6-O-methylerythromycin A are described in at least U.S. Pat. Nos. 4,331,803; 4,670,549; 4,672,109; and 4,990,602. For the convenience of the reader, the examples of known methods for preparing 6-O-methylerythromycin A are described below.

In one method, erythromycin A is converted to 2'-O-3'-N-bis(benzyloxycarbonyl)-N-demethylerythromycin A.

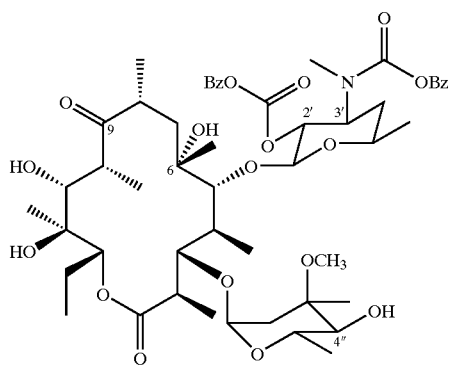

The 6-hydroxy group is methylated by reaction with an alkylating agent, such as bromomethane or iodomethane, and a base. Removal of the benzoyl groups by catalytic hydrogenation and reductive methylation of the 3'-position nitrogen atom gives 6-O-methylerythromycin A. See U.S. Pat. No. 4,331,803.

An alternative synthesis involves methylation of a 6-O-methylerythromycin A 9-oxime intermediate, which can be prepared by methods known in the art, such as reacting erythromycin A with hydroxylamine hydrochloride in the presence of base or by reaction with hydroxylamine in the presence of acid, as described in U.S. Pat. No. 5,274,085. Reaction of the oxime intermediate with a compound represented by the formula R—X, wherein R is allyl or an optionally substituted benzyl group and X is halogen, forms a quaternary salt. Methylation of the quaternary salt, followed by elimination of the R groups and deoximation gives 6-O-methylerythromycin A. Preferred methylating reagents are methyl bromide, methyl iodide, dimethylsulfate, methyl p-toluenesulfonate, methyl methanesulfonate, and the like. See U.S. Pat. No. 4,670,549.

Methylation of 6-O-methylerythromycin A oxime derivatives of formula:

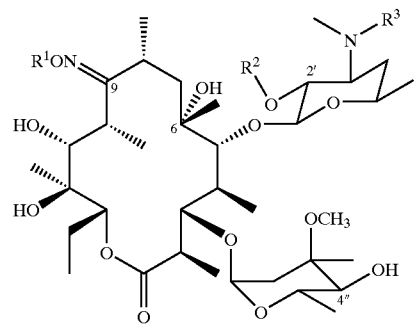

wherein $R^1$ is alkyl, alkenyl, substituted or unsubstituted benzyl, oxyalkyl, or substituted phenylthioalkyl, $R^2$ is benzyloxycarbonyl, and $R^3$ is methyl or benzyloxycarbonyl, followed by deprotection, deoximation, and reductive methylation when $R^3$ is benzyloxycarbonyl gives 6-O-methylerythromycin A. See U.S. Pat. No. 4,672,109.

A particularly useful preparation of 6-O-methylerythromycin A involves methylation of the oxime derivative,

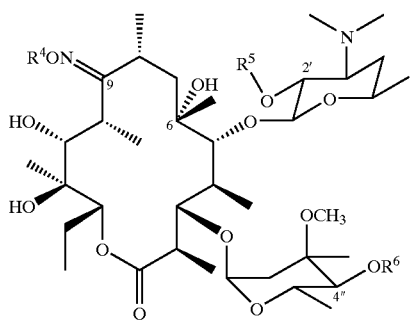

wherein $R^4$ is alkenyl, substituted or unsubstituted arylmethyl, or alkoxyalkyl, $R^5$ is substituted silyl, and $R^6$ is substituted silyl, or $R^6$ is H. Removal of the protecting groups and deoximation is then accomplished in a single step by treatment with acid to give 6-O-methylerythromycin A. See European Patent Specification 260 938 B1 and U.S. Pat. No. 4,990,602.

In a preferred route, a 6-O-methylerythromycin A compound can be obtained by oximating the erythromycin A; protecting the 9-, 2' and 4"-hydroxyl groups, either simultaneously or in sequence, with a hydroxyl protecting group; and reacting the compound obtained therefrom with the suitable alkylating agent. The protecting groups are then removed and the compound is deoximated to produce 6-O-methylerythromycin A. The preferred protecting groups are trimethylsilyl, tert-butyldimethylsilyl, and tert-butyldiphenylsilyl. When the protecting groups are substituted silyl, deprotection and deoximation can be accomplished in a single step by treatment with acid, for example using formic acid or sodium hydrogen sulfite. See U.S. Pat. No. 4,990,602.

Synthesis of 6-O-Methylerythromycin A Acetonitrile Solvate (Form III)

To prepare a Form III polymorph, the 6-O-methylerythromycin A is recrystallized in acetonitrile solvent. The 6-O-methylerythromycin A starting material can be obtained by any of the methods described above or by other methods which provide a stable, 6-O-methylerythromycin A compound.

The 6-O-methylerythromycin A starting material is suspended in a suitable amount of acetonitrile solvent. The amount of acetonitrile should be sufficient for dissolving the desired quantity of 6-O-methylerythromycin A. Preferably, a saturated solution of 6-O-methylerythromycin A is prepared in an acetonitrile solution heated to an elevated temperature near reflux. The solid 6-O-methylerythromycin A starting material is added to the hot solvent. The mixture can be stirred to obtain a homogenous solution. Heating of the suspension is continued until complete or nearly complete dissolution of the solid. Generally, the dissolution can be accomplished between about 10 minutes and two hours.

The mixture is filtered while hot to obtain a clear filtrate. In a preferred method, the filtration is accomplished in ambient conditions without a vacuum. The filtrate is slowly cooled until equilibrium is established with the ambient environment. For the purposes of this specification, an "ambient environment" or "ambient temperature" refers to temperatures from about 20° C. to about 25° C. at atmospheric pressure. The filtrate can be further cooled to a temperature from about 0° C. to about 5° C. to obtain a solid precipitate. The preferred method for cooling the filtrate is by using a non-insulated glass container partially immersed in an ice bath. Solid precipitates in the mixture can be removed from the filtrate in any suitable manner for isolating the solid. Most preferably, the solid is removed by known filtration methods, including vacuum filtration. The isolated solid corresponds to a substantially pure Form III acetonitrile solvate.

Preparation of 6-O-Methylerythromycin A Form II Crystal Structure via Form III The Form III acetonitrile solvate provides a useful intermediate for preparing the Form II crystal of 6-O-methylerythromycin A. At present, 6-O-methylerythromycin A Form II is the most widely marketed form of 6-O-methylerythromycin A.

The Form III acetonitrile solvate can be heated to elevated temperatures from about 100° C. to about 180° C. to convert the solvate into the Form II crystal structure. The Form III acetonitrile solvate is preferably heated in a calibrated convection oven. Controlled conditions in a calibrated vacuum oven can also be used. The conversion is typically carried out between atmospheric pressure and a pressure of about 2 inches of mercury. Conversion of the Form III solvate generally occurs between about 20 and 24 hours. Preferably, the Form III solvate is heated for about 1 to 2 days.

Figure 4:
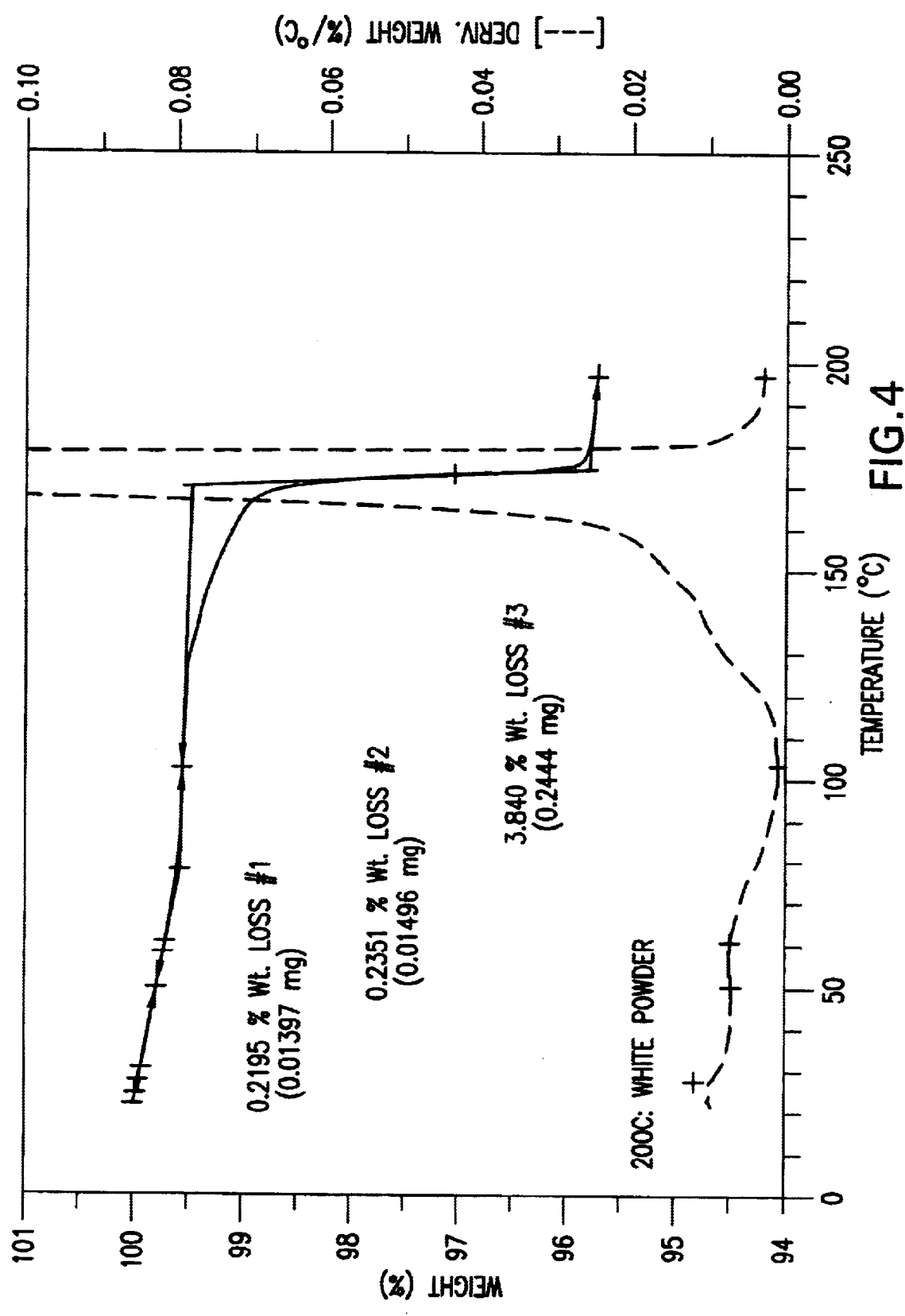
FIG. 4 is a graphical illustration of the thermogravimetric analysis (TGA) of the 6-O-methylerythromycin A acetonitrile solvate.

Suitable temperatures for the conversion of the Form III solvate to the Form II crystal structure of 6-O-methylerythromycin A can vary depending on the conditions of the reaction. As illustrated in FIG. 4, the thermogravimetric analysis spectrum, a 6 milligram sample of the Form III solvate can be converted to the Form II crystal structure at about 175° C. under purging with an inert gas, such as nitrogen, with an increase of 5° C. per minute. At atmospheric pressure, the preferred temperatures for the conversion of the Form III solvate to Form II are from about 80° C. to about 180° C. The more preferred temperatures for the conversion are from about 90° C. to about 105° C.

The Form II crystal structure can be incorporated into a pharmaceutically acceptable composition by methods previously described in the literature. Solid dosage forms for oral administration can be prepared to provide capsules, tablets, pills, powders and granules. In such solid dosage forms, the Form II crystal structure of 6-O-methylerythromycin A can be admixed with one or more inert excipients or carriers, for example, fillers, binders, humectants, disintegrating agents, disintegrating agents, solution retarding agents, absorption accelerators, wetting agents, absorbents, lubricants, and the like. Dosage forms for topical or transdermal administration can also be prepared and include, ointments, pastes, creams, lotions, gels, powders, solutions, sprays, inhalants, patches, and the like. Compositions for rectal or vaginal administration, such as suppositories, can also be prepared. More discussion relating to the compositions of 6-O-methylerythromycin A can be found, for example, in U.S. Pat. No. 4,331,803.

Characterization of the 6-O-Methylerythromycin A Acetonitrile Solvate

Solids from the recrystallization were prepared according to the methods described above and analyzed under standard conditions with a calibrated Scintag X-ray diffraction system. The wet solid demonstrated a powder X-ray diffraction pattern having the 2-theta angles 9.05±0.2; 9.64±0.2; 11.8°±0.2; 12.77±0.2; 15.28±0.2; 16.04±0.2; 16.55±0.2; 16.7±±0.2; 18.27±0.2; 18.79±0.2; and 24.94±0.2, which corresponds with the Form III powder X-ray diffraction pattern.

The wet solid was allowed to dry at room temperature. The air-dried sample was analyzed and the powder X-ray diffraction data was consistent with the powder X-ray diffraction pattern of a 6-O-methylerythromycin A Form III crystal structure. The air-dried sample was heated to a temperature between about 40° C. to about 45° C. in a calibrated vacuum oven for five days at atmospheric pressure. The solid obtained also exhibited a X-ray diffraction pattern consistent with a Form III crystal structure.

A wet solid sample obtained from the recrystallization was heated in a calibrated convection oven to a temperature between about 100° C. and 105° C. The resulting solid demonstrated an X-ray diffraction pattern having the following characteristic 2-theta angles: 8.52°±0.2, 9.48°±0.2, 10.84°±0.2, 11.48°±0.2, 11.88°±0.2, 12.36°±0.2, 13.72°±0.2, 14.12°±0.2, 15.16°±0.2, 16.48°±0.2, 16.92°±0.2, 17.32°±0.2, 18.08°±0.2, 18.40°±0.2, 19.04°±0.2, 19.88°±0.2, and 20.48°±0.2, which is consistent with the Form II crystal structure. The testing conditions and the corresponding result are summarized below in Table 1.

TABLE 1

| Sample # | Conditions | Analytical Result |
|---|---|---|
| 1 | wet solid | Form III spectra |
| 2 | air dried solid | Form III spectra |
| 3 | heat 40° C.–45° C., 5 days | Form III spectra |
| 4 | heat to 100° C.–105° C., 24 hours | Form II spectra |

Crystallographic data was obtained by solvate single crystal analysis using a Scintag XDS-2000 powder X-ray diffraction system. Samples for X-ray diffraction analysis were prepared by spreading the sample powder (with no prior grinding required) in a thin layer on the sample holder and gently flattening the sample with a microscope slide. A Scintag X-ray Diffraction system was used with the following parameters: X-ray source is CuKα; range is 2–35°; scan rate is 1.00 degree/minute; step size is 0.0300 degree; and wavelength is 1.54060 angstroms.

Characteristic powder X-ray diffraction pattern peak positions are reported for polymorphs in terms of the angular positions (two theta) with an allowable variability of ±0.2°. The variability of ±0.2° is intended to be used when comparing two powder X-ray diffraction patterns. To determine the range of angular positions, the measured peak is taken with its range of variability (i.e. ±0.2°). If a diffraction pattern from one peak overlaps with the diffraction pattern from the other peak, then the two peaks are considered to have the same angular position.

For example, if a diffraction pattern peak from one pattern is determined to have a peak position of 9.05°, for comparison purposes the allowable variability allows the peak to be assigned a position in the range of 8.85°–9.25°. If a comparison peak from the other diffraction pattern is determined to have a peak position of 9.20°, the allowable variability for comparison purposes can be assigned a position in the range of 9.00°–9.40°. The two peaks are considered to have the same angular position because the ranges of the peak positions (i.e., 5.10°–5.30° and 5.250–5.45°) for the peaks being considered overlap.

FT mid infrared analysis of samples was conducted in the following manner. Samples were analyzed as neat, undiluted powders. A Nicolet Magna System 750 FT-IR spectrometer with a Nic-Plan infrared microscope was used with the following parameters: the source was infrared; the detector was MCT/A; the beamsplitter was KBr; mirror velocity was 1.8988 centimeters/second, the aperture was 75.00; sample gain was 8.0; and the resolution was 4.000 centimeters $^{-1}$.

Differential scanning calorimetric analysis was conducted in the following manner. A T.A. Instruments Thermal Analyzer 3100 with Differential Scanning Calorimetry module 2910 was used along with DuPont 2100 DSC software version 4.0B. The analysis parameters were: sample weight 1.7100 milligrams, placed in a covered, uncrimped aluminum pan; heating rate was room temperature to 250° C. at 5° C./minute under a nitrogen purge.

Thermogravimetric analysis was conducted in the following manner. A T.A. Instruments Hi-Res thermogravimetric analyzer with Thermogravimetric Analyzer module 2950 was used along with DuPont 2100 TGA software version 5.1 A. The analysis parameters were: sample weight 6.3640 milligrams; heating rate was room temperature to 200° C. at 5° C./minute under a nitrogen purge.

The invention will be better understood in connection with the following Examples, which are intended as an illustration of and not a limitation upon the scope of the invention. Variations and changes which are obvious to one skilled in the art are intended to be within the scope and nature of the invention.

EXAMPLES

Example 1

Preparation of Form III 6-O-Methylerythromycin A

Crude 6-O-methylerythromycin (9.72 g, Abbott Laboratories, Abbott Park, Ill. U.S.A.) was dissolved in 100 mL of hot acetonitrile at 80° C. The mixture was filtered hot to obtain a clear filtrate, which was slowly cooled to room temperature, and then cooled to 0–5° C. The solids were collected by filtration and the wet cake was sampled (7.14 g).

The solid was allowed to dry at room temperature until the solvent evaporated. A sample was prepared for analysis by powder X-ray diffraction. The data confirmed that the sample was a Form III crystal structure of 6-O-methylerythromycin A.

Example 2

Preparation of Form III 6-O-Methylerythromycin A

The air dried sample from above, Example 1, was heated at 40–45° C. for five days and sampled. Powder X-ray diffraction data confirmed that the sample was Form III of 6-O-methylerythromycin A.

Example 3

Preparation of Form II 6-O-Methylerythromvcin A

The 6-O-methylerythromycin was dried at 100–105° C. in a standard, calibrated convection oven for one day. The resulting compound was allowed to cool and was characterized by powder X-ray diffraction analysis. The powder X-ray diffraction pattern of the dried compound confirmed that the compound was Form II of 6-O-methylerythromycin A.

What is claimed is:
1. An isolated crystal form of 6-O-methylerythromycin solvate having the formula:

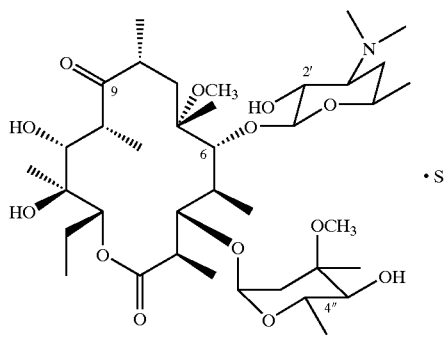
(I)

wherein S represents one to three molecules of acetonitrile solvent.

2. The solvate according to claim 1, wherein the powder X-ray diffraction pattern for the solvate exhibit the 2-theta angles 9.05±0.2; 9.64±0.2; 11.80±0.2; 12.77±0.2; 15.28±0.2; 16.04±0.2; 16.55±0.2; 16.70±0.2; 18.17±0.2; 18.79±0.2; and 24.94±0.2.

3. The solvate according to claim 1, wherein crystallographic unit cell parameters defined as a, b, c, and β form the crystallographic unit cell having the representative lengths 10.591 (1) Å; 18.036 (1) Å; 11.555 (1) Å; and β is 95.72 (1)° to afford a cell volume of 2196.2 (3) Å$^3$.

4. A method of preparing a crystalline 6-O-methylerythromycin acetonitrile solvate, comprising the steps of:

a.) treating 6-O-methylerythromycin with acetonitrile to obtain a homogeneous solution;

b.) allowing the solution to equilibrate at ambient temperature;

c.) cooling the solution to a temperature of 0–5° C. to form a solid precipitate in solution; and d.) collecting the solid precipitate to isolate a 6-O-methylerythromycin acetonitrile crystal structure.

5. A method for preparing 6-O-methylerythromycin crystal form II, comprising drying a 6-O-methlerythromycin acetonitrile solvate having the formula:

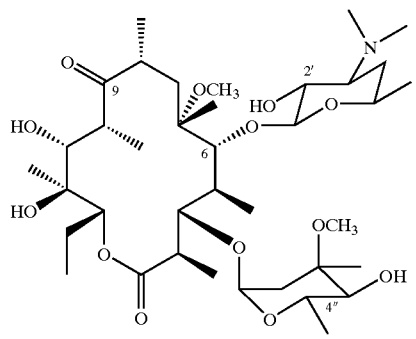
(I)

wherein S represents one to three molecules of acetonitrile solvent, at a temperature from about 80° C. to about 180° C. and isolating 6-O-methylerythromycin crystal form II.

6. The method according to claim 5, wherein the 6-O-methylerythromycin acetonitrile solvate is heated to a temperature from about 90° C. to about 105° C.

* * * * *